United States Patent [19]

Roush et al.

[11] Patent Number: 5,038,795
[45] Date of Patent: Aug. 13, 1991

[54] MUSCLE TONOMETER APPARATUS AND METHOD

[76] Inventors: Elsie S. Roush, 10 Babler La., St. Louis, Mo. 63124; James H. Hahn, 1225 Danvers St., St. Louis, Mo. 63146; James W. Meeks, 712 E. Monroe Ave., St. Louis, Mo. 63122

[21] Appl. No.: 551,179

[22] Filed: Jul. 10, 1990

Related U.S. Application Data

[63] Continuation of Ser. No. 82,058, Aug. 5, 1987, abandoned.

[51] Int. Cl.[5] .............................................. A61B 5/103
[52] U.S. Cl. ................................................ 128/774
[58] Field of Search ............................... 128/774, 778

[56] References Cited

U.S. PATENT DOCUMENTS

| 4,132,224 | 1/1979 | Randolph | 128/774 |
| 4,432,376 | 2/1984 | Huszar | 128/774 |

FOREIGN PATENT DOCUMENTS

1132913  1/1985  U.S.S.R. ............................ 128/774

Primary Examiner—William E. Kamm
Assistant Examiner—Kennedy J. Schaetzle

[57] ABSTRACT

Apparatus for use in measuring the muscle tone of a muscle comprising a force applying assembly operable by a user to apply variable forces to a muscle to effect displacements of the muscle in accordance with the amount of force applied, transducers for detecting the amount of force being applied to the muscle and the muscle displacement caused by such applied force and for producing force and displacement signals, electronic circuitry for deriving from a number of force displacement signals produced within a linear elastic region of force/displacement curve to produce a muscle tone measurement, and a display for displaying the muscle tone measurement.

15 Claims, 6 Drawing Sheets

MUSCLE TONOMETER APPARATUS AND METHOD

BACKGROUND OF THE INVENTION

This is a Continuation of Copending application Ser. No. 82,058, filed Aug. 5, 1987, now abandoned in the names of the present inventors.

The present invention relates generally to an apparatus and method for quantifying skeletal muscle tone and more particularly to a compact electro-mechanical instrument which accurately measures skeletal muscle tone of low tone, normal tone, and high tone muscle groups. The present apparatus measures the full range of muscle tone and produces a numerical value readout on the apparatus representative of such tone. This numerical value has been calculated in grams/centimeters (gm/cm) times a constant (k) dependent upon the type of subject being measured, such unit of measurement for muscle tone (gm/cm×k) being defined as a Roush.

DESCRIPTION OF RELATED ART

There exists an increasing need in the medical research and diagnostic arts for an instrument adapted to quantify the tone of a muscle body while the muscle body is at rest or undergoing varying degrees of stimulation. Muscle tone is defined as the normal tension in a muscle body or the muscle body's natural resistance to stretching. Quantifying muscle tone is important in many areas of physiological research and clinical diagnosis. Specifically, quantifying muscle tone can further the study of muscle operation; show the effect of physical fitness theories that have been applied to muscle bodies; and enable doctors and researchers to better understand the cause of bone loss and other physiological changes, including the bone loss and other physiological changes experienced by astronauts in space under zero gravity conditions. The instrument of the present invention quantifies muscle tone by measuring the elasticity of the muscle under study. "Elasticity" is defined as "the inherent property in bodies to recover to a former state after a force of an external pressure, tension or distortion has been removed". It is the measurement of this inherent recovery property, that is, the measurement of a muscle body's "spring rate", that is important in quantifying muscle tone. This tone or "spring rate" is maintained by minute neuro-muscular reflexes.

One prior art device is described in Huszar U.S. Pat. No. 4,432,376 which discloses a method and apparatus for determining the extensibility of selected non-excised visceral tissue of the uterine cervix, the ear or skin. A method is disclosed in the Huszar patent for calculating an extensibility curve for various tissues, and primarily for cervical tissue during pregnancy and labor. "Extensibility" is defined in the patent as the maximum degree of distension that a tissue may undergo before the tissue tears. The cervical instrument disclosed in the Huszar patent includes a scissors-like apparatus having two forwardly extending outer arms connected at a pivot, each outer arm having a probe element mounted to an inner surface thereof. The probe elements are mounted such that they operatively contact opposite surfaces of the anterior or posterior lip of a cervix. When in contact with the cervical lip the probe elements are moved toward one another by applying compressive force to the outer arms.

The Huszar apparatus is utilized by applying either a constant force or a series of increasing forces to the probe elements.

The method disclosed in Huszar compares the amount of displacement of the probe elements relative to each other with the corresponding amount of force applied to the probe elements, and then determines or calculates an instantaneous quotient of the displacement to the force applied. The quotient is then plotted or displayed as a function of time when a constant force is applied to the probe elements, or as a function of the force applied when variable forces are applied to the probe elements. A plot of a series of such quotients represents a modulus curve of extensibility from which an operator or doctor is able to determine, based upon his experience and background knowledge, when the tissue is at or near its tearing limit.

The Huszar apparatus and method are therefore used to develop a plot or display to indicate the extent to which a tissue may be stretched before the tissue tears apart, the plot or display being totally dependent upon time. This is important because the numerical muscle tone value derived through the use of the instrument of the present invention is not dependent upon time.

At the present time, the main stumbling block for diagnosticians and researchers who are studying a skeletal muscle body's normal tension or resistance to stretching, is their inability to reduce the complex phenomena of muscle tone into a simpler entity, a verifiable quantity, through the use of a simple quantitative assessment instrument. The size and inadequate sensitivity of existing muscle tone assessment instruments, which generally take the form of large, non-transportable machines which lack the sensitivity necessary to assess muscle tone in a hypotonic or low tone state. Such prior art instruments have therefore been inadequate for testing muscle bodies in their resting states.

The inadequate nature of the prior art muscle tone assessment instruments for most research and diagnostic purposes, especially with respect to tone assessment of muscle bodies in their hypotonic or resting state, has forced researchers and diagnosticians to rely on manual assessment of muscle tone in such states. However, existing manual muscle tone assessment techniques are highly subjective and do not provide a quantifiable, and therefore verifiable, evaluation of a muscle body's tone. Existing manual techniques include palpation of the muscle body, assessing "the feel" of resistance while passively stretching the muscle body, and visually observing an animal body in selectively-arranges postures.

The need for an instrument capable of quantitatively assessing the tone of a skeletal muscle is great because muscle tone provides the background or base upon which purposeful motor movements are superimposed, and muscle tone may also serve as a precursor of confirmation indicator of several genetic and environmental maladies.

An objective quantification of muscle tone, such as that provided by the tonometer instrument of the present invention, has application in many areas, including, by way of illustration only and not by way of limitation, the following examples.

First, the present tonometer instrument facilitates the identification of both low muscle tone, or hypotonicity, and losses in muscle tone. The identification of a state of low muscle tone is important in studying genetic deviations in musculature, such as the deviations found in persons afflicted with Down's syndrome. Gradual loss of muscle tone has also been found to occur in individuals afflicted with any one of a variety of neuromuscular diseases. Providing means to quantify the decrease or absence of muscle tone not only facilitates diagnosis of such diseases and/or genetic defects, but also serves as a means to ascertain improvements resulting from utilizing various treatment procedures, such as providing before and after drug therapy measures as well as ascertaining the effectiveness of any therapeutic intervention.

Second, the tonometer instrument of the present invention has apparent value in evaluating ensuing bone loss, muscle tone declines, and other physiological changes occurring in the musculature, skeletal and nervous systems of persons subjected to conditions of weightlessness, such as astronauts travelling in outer space. Evaluations of such persons' muscle tone has important application with respect to the exploitation of outer space resources and in interplanetary travel. The ability to quantify such losses and declines would further research into preventative programs and facilitate quicker resolutions of such muscle loss and bone loss problems.

Third, by permitting objective quantified evaluation of all ranges of the tone of muscle bodies, at zero gravity through full contraction, the present tonometer instrument could permit the boundaries of various research frontiers to be extended and expanded. Applications could be found in sports medicine, pediatric care and development, and geriatric care, all because changes in muscle tone could be quantified an easily studied, and could be used in establishing improved muscle development programs.

Fourth, the present tonometer instrument provides an extensive evaluation of the tone of a muscle body and thereby facilitates continuous assessments of therapy programs and more rapid diagnoses of muscle-affecting diseases.

Fifth, the tonometer instrument of the present invention provides a new dimension in preventative medicine, and it is foreseeable that muscle tone measurements and evaluations will be incorporated into routine physical examinations.

Additionally, the tonometer instrument of the present invention could be easily adapted for use in animal experimentation, including the study of muscle formation and feed-lot growth of livestock, which could lead to leaner, more efficiently grown animals to supply meat for public consumption.

Therefore, a principal object of the invention is to provide a muscle tonometer instrument and method for objectively measuring the tone, or resistance to compression, of a muscle body.

Another object is to provide such an instrument and method for quantifying muscle tone by applying a known force to a muscle body, and measuring the relative amount of compression of the muscle body caused by the force application.

An additional object is to provide a means to enable experimentation and assessment of muscle tone when the muscle body is in a hypotonic or resting state.

Another object is to provide a means to facilitate assessment of physical therapy programs by determining the effect of such therapy programs on muscle tone.

A still further object is to provide a means that will facilitate quicker confirmation and/or diagnosis of genetic and other maladies by determining changes or absence of changes in muscle tone over a period of time.

An additional object is to provide a means that will facilitate the study of the effects of weightlessness or "zero gravity" on muscle tone and/or bone structure.

Still another object is to provide a means that will facilitate the study of growth techniques in animals and the effect of such techniques on growth efficiency of feed livestock.

The tonometer instrument of the present invention facilitates a wide range of analytical and diagnostic applications through the relatively simple measurement of the "spring rate" or elasticity of muscle tissue, with the "spring rate" being defined as the quotient of the change in external force applied to the muscle body divided by the change in displacement, or compression, of the muscle tissue that results from such change in external force. In practice, it has been found that muscle displacement or compression measurements can be obtained by measuring relative positions of caliper-like members squeezably applied to opposite sides of the muscle and that force measurements can be obtained by measuring the bending or strain of such caliper-like members.

SUMMARY OF THE INVENTION

A tonometer instrument which comprises a body portion that includes means for applying a force to a portion of a muscle group to be studied, such force applying means generally comprising a pair of calipers extending from the body portion and capable of relative movement toward and away from each other; means for measuring both the relative amount of force applied to the muscle group and the resultant displacement of the muscle group, such measuring means generally including means for converting the force and displacement measurements into electronic signals; electronic circuit means for deriving a muscle tone measurement from a plurality of force and displacement measurements and means for displaying the derived muscle tone measurement.

DETAILED DESCRIPTION OF THE ILLUSTRATED EMBODIMENTS

Figure 4:
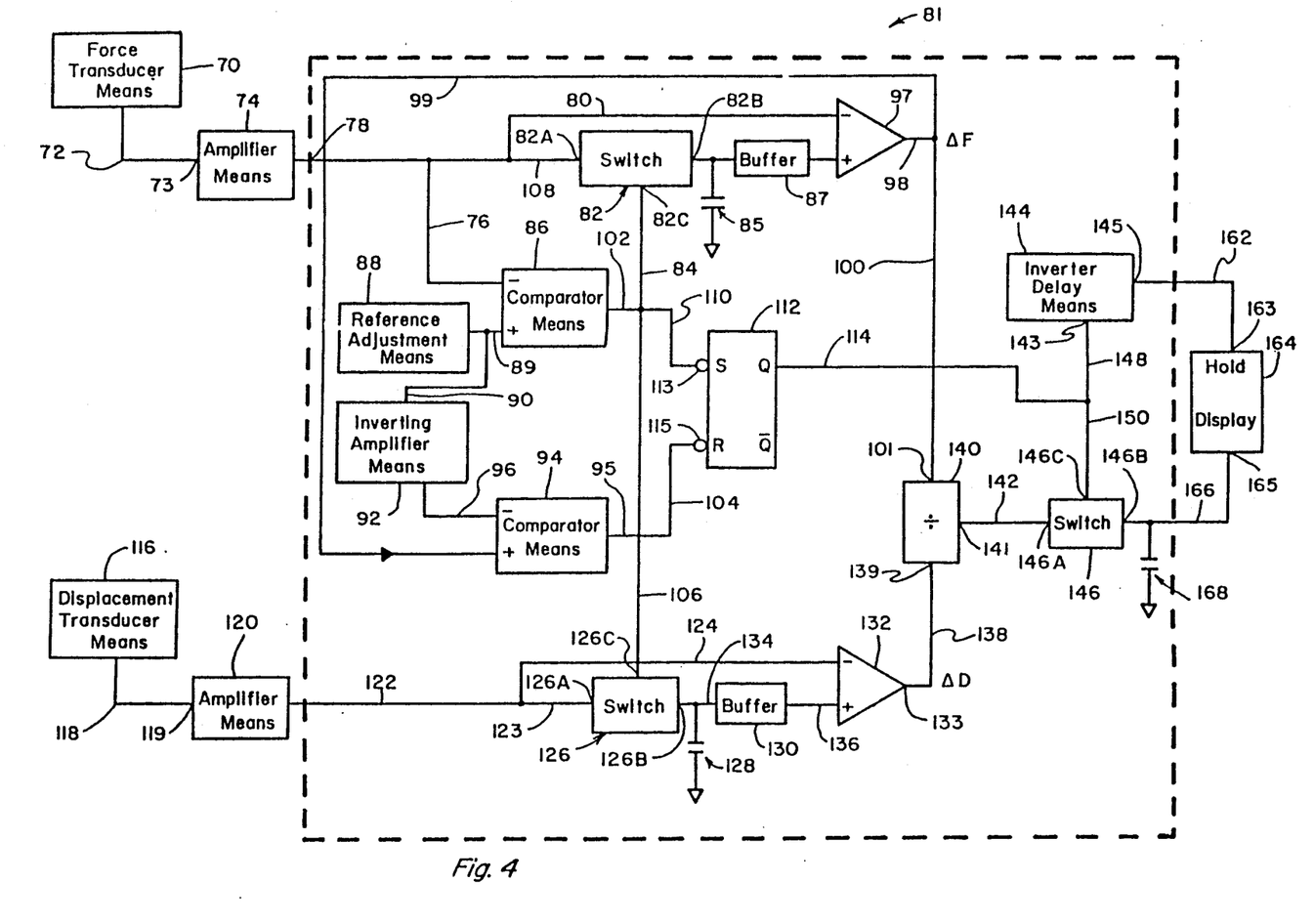
FIG. 4 is a block diagram depicting the electronic circuitry of a preferred embodiment of the invention.
Figure 5:
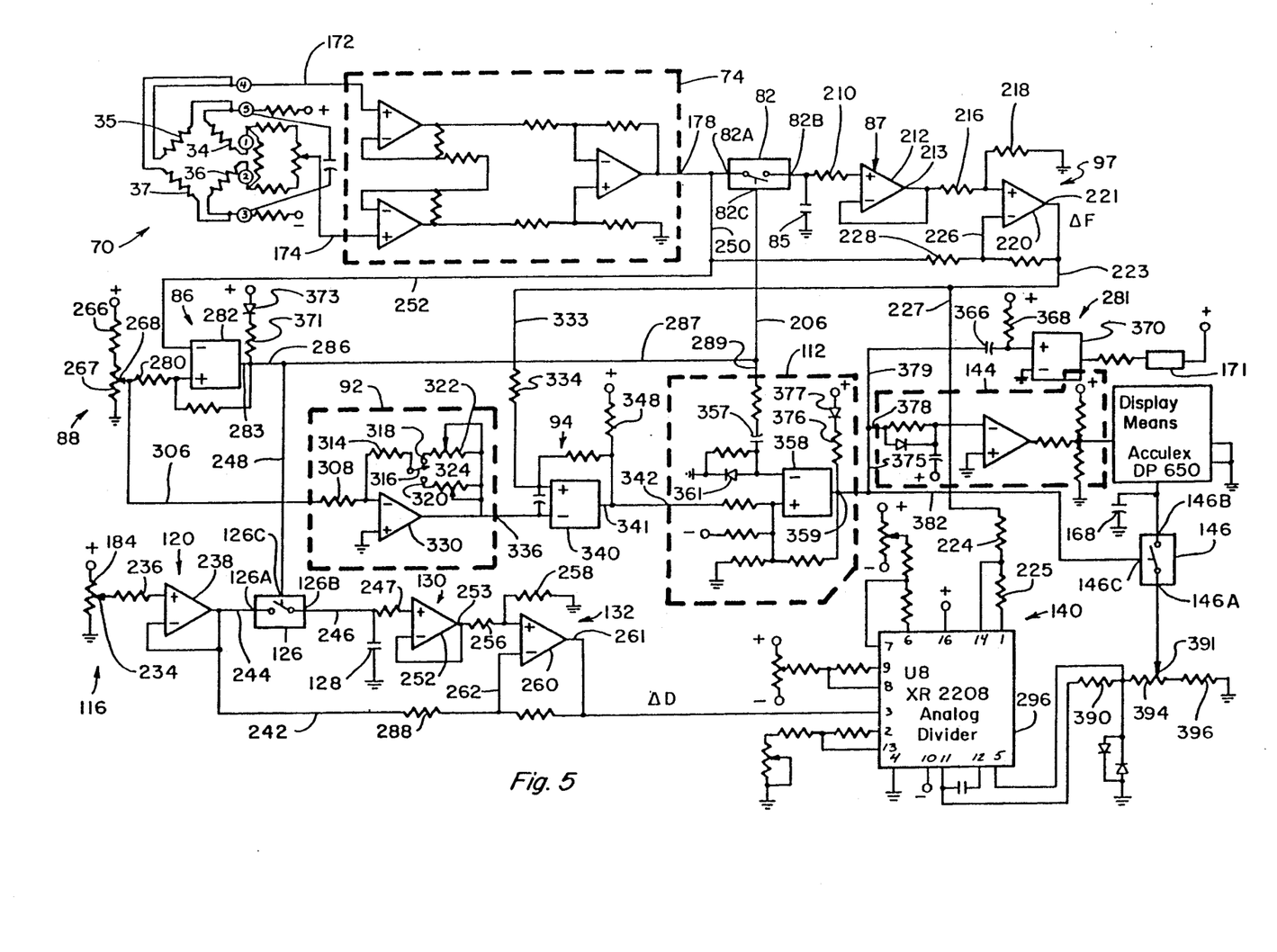
FIG. 5 is a detailed schematic circuit diagram corresponding to the block diagram of FIG. 4.

The electronic circuitry of one embodiment of the invention shown, for example, in FIGS. 4 and 5, is designed to utilize empirical information obtained from a variety of muscle tone studies on various muscle types previously conducted by Dr. Elsie Roush, one of the co-inventors of the present invention. It has been found in such studies that when an identical compression force is applied to respective muscles, different respective muscle displacements result, depending upon the muscle tone of the particular muscle to which the force is applied. The ratio of the change in applied force to the resultant change in displacement for any given muscle is generally acknowledged by those familiar with such studies to be an indicator of the muscle tone of such muscle. When the displacement of a given muscle is charted over a range of forces applied thereto, and the resulting graph is compared with similar graphs for like and unlike muscle types, it can be observed from the curves of such graphs that three distinct regions of interest, corresponding to three distinct muscle compression regions, are experienced as an increasing amount of force is applied to a muscle.

Figure 1:
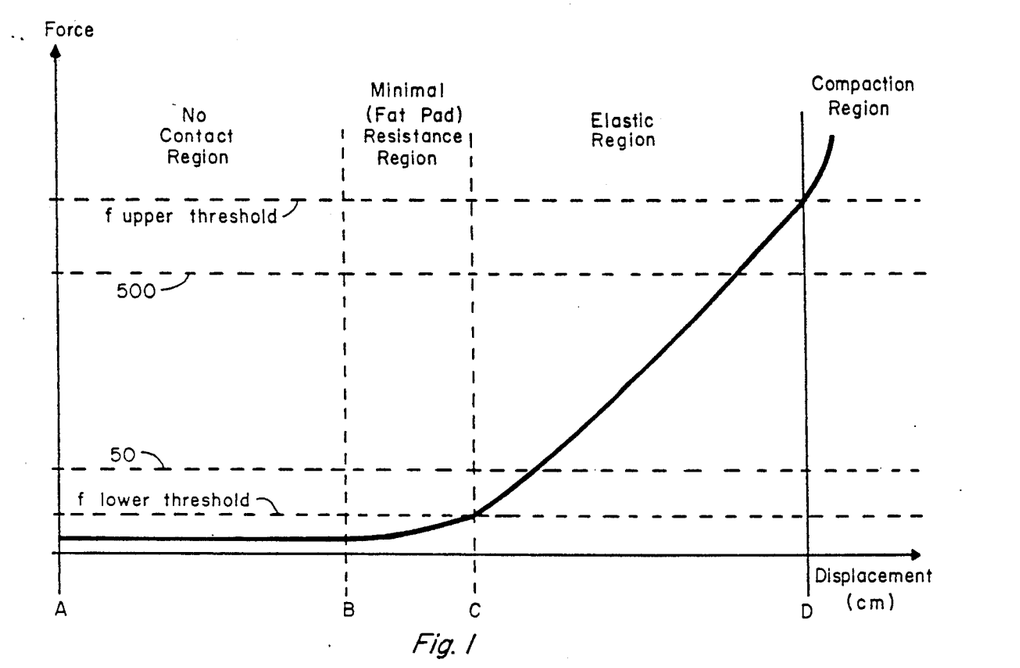
FIG. 1 is a graph of representative force-displacement measurements for a hard muscle.

As shown in FIG. 1, the regions of interest include a minimal resistance region of the muscle, corresponding to the graph curve between points B-C, the elastic region of the muscle, corresponding to the graph curve between points C-D, and the compaction region of the muscle, corresponding to the graph curve beyond point D. That portion of the graph between points A-B depicts force-displacement measurements obtained as the caliper tongs are being displaced sufficiently to be moved into initial contact with the muscle (point B) and no force is yet being applied.

In the first region of interest (region B-C), the muscle exhibits a relatively small (but progressively greater) resistance as increasing force is applied thereto. In such region the dermal fat pad portion of the muscle is being compressed. Such dermal fat pad portion of the muscle is known to have a low elasticity.

Once sufficient force is applied to the muscle to move past the fat pad, the second, or elastic, region (region C-D) of the muscle is encountered, in which region accurate readings of the muscle elasticity can be obtained. Studies by Dr. Roush have indicated that, when a preferred embodiment of the present invention is utilized, regardless of the thickness of the fat pad portion of the muscle, the elastic region of the muscle is encountered when the applied force exceeds about 50 grams. An applied force greater than such force (and, as will be explained further hereinafter, less than a maximum force) provides a stimulation of neuro-muscular receptors deep within the tissue, causing a reflex response. Such reflex response is minute and not visibly apparent, but is similar to the gross reflex that results when a tap of the physician's hammer to the tendon of a muscle causes a gross jerk, as in the knee jerk reflex. The gross reflex results in a contraction of the entire muscle. The minute reflex results in contraction of small groups of cells and is comparable to the ongoing stimulation that is ever-present in the muscle when the nerve is intact. It is the minute reflex that maintains muscle tone at rest, and at zero-gravity.

The noted studies by Dr. Elsie Roush also have indicated that a maximum force value exists for the elastic region, and that when forces in excess of such value are applied, the compaction region of the muscle (region beyond Point D) is encountered. As will be further explained hereinafter, the data applicable to such compaction region is unreliable for purposes of deriving accurate muscle tone measurements, and it is therefore necessary to avoid the use of such data. Empirically, it has been found that the unreliable data of the compaction region can generally be avoided by utilizing for muscle tone measurement purposes only that data obtained, for low tone muscles, below an upper force threshold value of about 100 grams and, for high tone muscles, below an upper force threshold value of about 500 grams.

In the compaction region (the region beyond point D in FIG. 1), the application of progressively greater force results in little, if any, further compression of the muscle, and as a consequence the data applicable to such region cannot be relied upon to yield accurate muscle tone calculations. Compaction results in the takeover of different receptors (presso-receptors), as a consequence of which the minute reflexes discussed with respect to the elastic region of the muscle cannot fire off. As an aid to understanding this, it may be appreciated that when the skin is lightly touched, touch receptors send a message to the brain, but when the skin is squeezed, a takeover of presso-receptors (or even pain receptors) results and the touch pathway gives way to the stronger stimulus. It should be appreciated that a "soft" muscle (low tone) may experience a "squeezing" at a force lower than that at which a "hard" muscle (high tone) may experience a "squeezing".

The electronic circuitry of FIGS. 4 and 5 measures the amount of force applied to a muscle and is so designed, constructed, and/or programmed, to effect force-displacement ratio calculations in the elastic region of the muscle, i.e., between lower and upper force threshold values, to determine the muscle's spring rate, and to then display such spring rate, the final displayed value being defined to be the measured muscle tone. The unit of measurement of this final displayed value is in gm/cm×k, and is defined as a Roush. No further readings or analyses are required.

Figures 2, 3:
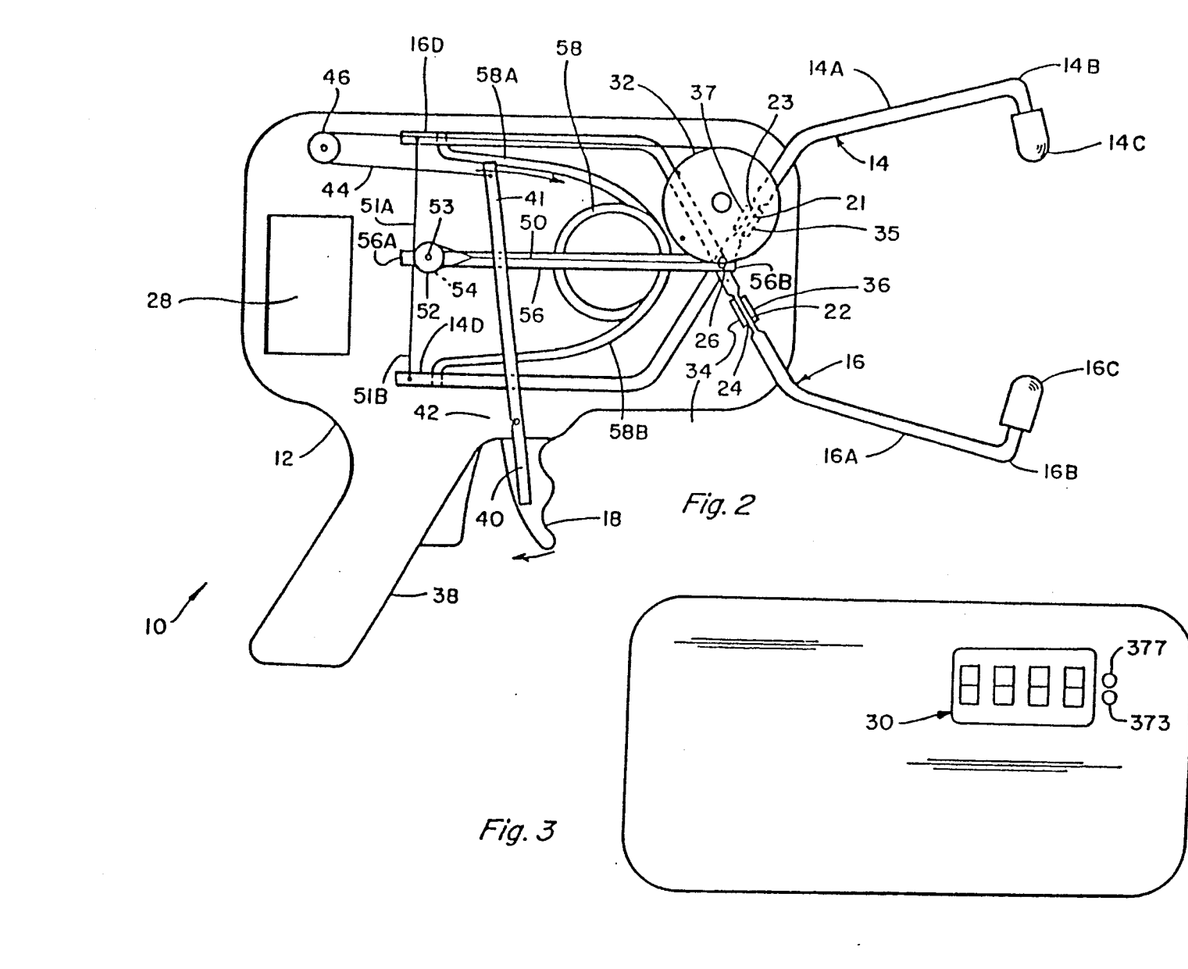
FIG. 2 is a diagrammatic right side view of a preferred embodiment of the mechanical elements of the present invention illustrating the general positioning and operation of such mechanical elements.
FIG. 3 is a plan view of a left panel of the embodiment of FIG. 2 showing the display means associated therewith.

The mechanical details of the presently preferred embodiment of the instrument of the invention are shown in FIG. 2. The instrument, designated generally as 10, is preferably constructed to be a compact, self-contained, portable, hand holdable unit, including a gun-shaped housing 12, which incorporates all necessary electrical and mechanical components Sufficient space is provided within housing 12 for the placement of the various mechanical elements that will subsequently be discussed, as well as for a battery or power unit 28, and for the circuitry. A display 30 (FIG. 3) is preferably mounted on the housing of the instrument for displaying the muscle tone value derived through the use of the instrument. The display 30 may include either or both visual and aural components, such as a light-emitting diode display, a liquid crystal display, or other suitable visual displays, and/or enunciators, horns, buzzers, or other suitable aural instruments.

The mechanical components include a pair of elongated tong or caliper arms 14 and 16 operatively assembled and positioned to open and close in a scissors-like motion in direct response to the application and release of pressure to a trigger mechanism 18, as will be explained in greater detail. Each caliper arm 14 and 16 includes a respective muscle contactor portion 14A, 16A which extends outwardly from the housing 12 and has a respective inwardly turned L-shaped bend 14B, 16B, as shown, near the outer end thereof, with a respective tong cap 14C, 16C mounted thereupon. Such tong caps provide surfaces for comfortably contacting a muscle when the caliper arms are operated to apply a compressive force to such muscle.

Each caliper arm includes on its muscle contactor portion an area of reduced cross-section near a caliper pivot pin 26, such as the flat, opposed surfaces 22 and 24 on tong arm 16 and the flat, opposed surfaces 21 and 23 on tong arm 14. Provided on such flat surfaces of the tong arms 14 and 16, one to a surface, are the sensor legs 34, 35, 36 37 (FIGS. 2 and 5) of a Wheatstone bridge strain gage transducer 70 (see FIGS. 4 and 5). Such types of strain gage transducers measure the "bending" of the caliper arms as a muscle is compressed therebetween and convert such measurement to an output analog voltage signal. This measurement is proportional to the force applied to the muscle body. It should be noted that the structural embodiment and the associated wiring of the transducers are not shown in FIG. 2. Such components as well as the circuitry for deriving the force displacement quotient will be subsequently detailed.

Squeezing trigger mechanism 18 toward hand grip 38 causes the trigger arm 40 engaged therewith to pivot on trigger pivot pin 42, thereby moving the top portion 41 of the trigger arm 40 forward. Such motion pulls a trigger cord 44, one end of which is attached to the top portion 41 of trigger arm 40, an intermediate length thereof which is looped around a rear idler pulley 46, and the opposite end of which is wrapped around and connected to pulley 32, thereby causing the pulley to rotate in a counterclockwise direction. In the preferred embodiment of the present invention, pulley 32 forms part of a displacement transducer 116 (FIGS. 4 and 5) that converts rotational movement of the pulley 32 into an output analog signal, as will be further explained hereinafter.

The counterclockwise rotation of such pulley 32 causes a tong cord 50, one end of which is attached to such pulley 32, to be wound thereupon. Tong cord 50, like trigger cord 44, is terminated on the pulley 32 to eliminate slippage during mechanical operation of the device. The opposite end of the tong cord 50 is connected in common to the ends of both of arm pull cords 51A and 51B. An intermediate length of cord 51A is looped around a tong pulley 52 mounted on the near side of pulley bar 56 on a shaft 53 attached to the bar 56 near the rear end 56A thereof, the forward end 56B of which bar 56 is connected to the caliper arm pivot pin 26. The opposite end of cord 51A is connected to the rear end 16D of caliper arm 16. Similarly, an intermediate length of cord 51B is looped around a tong pulley 54 mounted on the same side of pulley bar 56 on shaft 53 between tong pulley 52 and the bar 56. The opposite end of such cord 51B is connected to the rear end 14D of caliper arm 14. As tong cord 50 is wound upon pulley 32, the rear ends 14D and 16D of the two tong arms 14 and 16 are thus caused to be pulled toward each other, against the pressure being exerted thereupon by arm portions 58A and 58B of spring 58, which spring is provided to normally maintain the caliper arms in an open, spaced apart position when no pressure is being applied to trigger 18.

Optionally, an additional, relatively weak spring (not shown) could be so connected to the trigger arm 40 to counter the effect of spring 58 just sufficiently enough to ensure that tension is maintained on cords 44, 50 and 51A and 51B.

The strain gage sensors 34, 35, 36, 37 (FIGS. 2 and 5) positioned on the flat surfaces 21-24 of the tong arms measure the stress and strain applied by the tong heads and caused by minute deflections of the tong arms. Resistive force between the tong caps 14C and 16C causes deflection of both arms 14 and 16 at the flat surfaces thereof, which deflection is directly proportional to the resistive force. The preferred embodiment of the invention includes a Wheatstone bridge strain gage transducer with each sensor taking the form of a resistive element forming part of each leg of the bridge circuit. The resulting stretching or compression of the sensors due to the detected force results in a change in the electrical resistance of the corresponding leg of the Wheatstone bridge. Such change in resistance results in a corresponding change in the analog output voltage signal of the bridge circuit.

The displacement or change in distance between the tong arms is measured and translated by the pulley 32 into an analog voltage signal in the following manner. The rotational movement of the pulley as a result of movement of the tong arms, which is caused by moving the trigger 18, results in a change in the position of a slider arm of a conventional potentiometer, which action changes the ratio of the output resistance to the total resistance in a voltage divider network. The amount of voltage change is directly proportional to the linear displacement of the tongs.

As has been indicated earlier, and as will subsequently be discussed more fully, the force and displacement signals produced by the Wheatstone bridge strain gage transducer, and by the displacement transducer are applied to circuitry within housing 12. This circuitry calculates a ratiometric quotient $\Delta F/\Delta D$ that, for measurements within the elastic region of the muscle under study, corresponds to the elasticity of that muscle and is defined to be a measurement of the muscle tone of the muscle.

Referring now to FIG. 4, block 70 indicates generally the force strain gage transducer described earlier herein with reference to FIG. 1, which transducer measures the amount of applied force being exerted on the muscle body when such muscle body is positioned between the tong arms and force is being applied thereto. The force strain gage transducer 70 outputs an analog signal that is provided via lead 72 to input 73 of an amplifier 74 Such amplifier operates to amplify the signal provided thereto, and the amplified force signal output therefrom is provided to several locations, including via leads 78 and 80 to the inverting (−) input of a differential amplifier 97; via leads 78 and 76 to the inverting (−) input of a comparator 86; and via leads 78 and 108 to the first side 82A of a switch 82.

A reference voltage signal corresponding to a lower force value at or above the lower threshold force value of the elastic region may be established by reference adjustment means 88, and is provided via lead 89 to the positive (+) input of a voltage comparator 86, the output of which comparator 86 is provided to several locations, including via leads 102 and 84 to the actuation or control, input 82C of switch 82; via leads 102 and 106 to the actuation, Or control input 126C of a switch 126; and via leads 102 and 110 to the set (S) input of a flip flop 112. The switches 82 and 126 open and close in response to the state of the output signal from comparator 86, as will be more fully explained.

The reference voltage signal established by reference adjustment means 88 is also provided via lead line 90 to an inverting amplifier means 92 which amplifies such signal and outputs the resulting inverted amplified voltage signal via lead 96 to the negative (−) input of a voltage comparator 94, the positive (+) input of which comparator 94 is connected to the output 98 of differential amplifier 97 via lead 99 and the output 95 of which is connected via lead 104 to the reset (R) input of flip-flop 112. Inverting circle 113 positioned at the set input to flip-flop 112 and inverting circle 115 positioned at the reset input to flip-flop 112 indicate a LO true condition, i.e., the flip-flop inputs are only triggered by LO-going signals. The absolute value of the inverted amplified voltage signal from inverting amplified 92 may, because of the design of the embodiment of FIG. 4, be considered to be the equivalent of or to correspond to an upper force value above the value of the lower force value associated with the reference voltage signal established by reference adjustment means 88 and at or below the upper threshold force value at the elastic region.

The output side 82B of switch 82 is operatively connected to a signal storage means, such as capacitor 85, which acts to hold or store the signal provided thereto through switch 82. Optionally, a buffer 87 may be provided between the signal storage means and the inverting (−) input of differential amplifier 97. Differential amplifier 97 is a classic differential amplifier which operates to provide at output 98 a difference signal dependent upon the signals present upon such amplifier's inputs, which difference output signal is provided via lead 100 to the dividend input 101 of analog divider means 140 and, as has previously been discussed, via lead 99 to the positive (+) input of comparator 94.

Block 116 indicates generally the displacement transducer 32 of FIG. 2. Such transducer outputs an analog displacement signal which is provided via lead 118 to input 119 of an amplifier 120, the amplified output signal of which is provided via leads 122 and 124 to the inverting (−) input of a differential amplifier 132 and via leads 122 and 123 to the first side 126A of switch 126. The second side 126B of such switch is operatively connected to a signal storage means, such as capacitor 128, that acts to hold or store the signal provided thereto through switch 126. Optionally, a buffer 130 may be provided between the signal storage means and the non-inverting (+) input of differential amplifier 132. Like differential amplifier 97, differential amplifer 132 is a classic differential amplifer which operates to provide at output 133 a difference output signal dependent upon the signals present upon such amplifier's inputs, which difference output signal is provided via lead 138 to the divisor input 139 of analog divider 140.

Such divider 140 operates to produce at its output 141 a ratio output signal corresponding to the value of the signal present at input 101 thereof divided by the signal present at input 139 thereof, which ratio output signal is provided via lead 142 to the first side 146A of a switch 46. Switch 146 opens and closes in response to the state of flip-flop 112, the Q output of which flip-flop is connected via leads 114 and 150 to the actuation or control input 146C of switch 146 and via leads 114 and 148 to the input 143 of an inverter-delay means 144, the output 145 of which is provided via lead 162 to a trigger or hold input 163 of display 164. The second side 146B of switch 146 is operatively connected to a signal storage means, such as capacitor 168, which acts to hold or store the signal provided thereto through switch 146 and to provide such signal via lead 166 to the data input 165 of display 164.

It will be recognized that many different types of displays could be readily employed with the present invention. For present purposes, the display 164 may be considered to be any suitable display means capable of producing a display output, generally visual in nature, the displayed value of which corresponds to the data being supplied to a data input when the display is triggered by an appropriate trigger signal, such as a change in state of the signal being applied to a trigger input 163. Typical of a display which operates in such a manner is the Acculex DP 650 digital panel display.

It will be appreciated by those skilled in the art that the voltage comparators 86 and 94 operate in such a way that a HI output is produced whenever the voltage signal present on the positive (+) input thereof is greater, i.e. more positive, than the voltage signal present on the negative (−) input thereof, and that a LO output is produced whenever the voltage signal present on the negative (−) input thereof becomes greater, i.e., more positive, than the voltage signal present on the positive (+) input thereof. Typical of such types of comparators are those voltage comparators included on LM339chips, as will be further discussed with respect to FIG. 5.

It will be further appreciated that the reference adjustment means 88 may be so adjusted, prior to use of the tonometer device for obtaining muscle tone measurements, to establish a reference voltage signal of such a value that the output of voltage comparator 86 will remain HI until such time as the force detected by the Wheatstone bridge strain gage transducer is a force value at or above the lower threshold force value of the elastic region of the muscle to be studied.

In light of the foregoing, it will be understood that, so long as the output of voltage comparator 86 remains HI, i.e., so long as the force applied to the muscle under study is below a force value $f_{min}$ established to be at or above the lower threshold force value of the elastic region of the muscle under study, HI signals will be maintained at the control outputs 82C and 126C of switches 82 and 126 at the set (S) input of flip-flop 112. The HI signal at the control inputs 82C and 126C of switches 82 and 126 cause such switches to be maintained in a closed state, as a consequence of which the signals provided to the first sides 82A and 126A of such switches are communicated therethrough to the second sides 82B and 126B thereof. The amplified force signal communicated from the first side 82A of switch 82 to the second side 82B thereof charges capacitor 85 and is applied to the non-inverting (+) input of differential amplifier 97 through buffer 87. Since the amplified force signal from amplifier means 74 is also being provided via leads 78 and 80 to the inverting (−) input of differential amplifier 97, such differential amplifier operates at such time to produce at output 98 a difference output signal $\Delta F$, of essentially zero, which difference output signal is provided via lead 99 to the positive (+) input of voltage comparator 94 and via lead 100 to the dividend input 101 of divider means 140.

As has previously been discussed, the reference voltage signal established by reference adjustment means 88 is also provides to inverting amplifier 92, which amplifier operates to produce a negative voltage signal that is provided via lead 96 to the negative (−) input of voltage comparator 94. Since the difference output signal $\Delta F$ provided from output 98 of differential amplifier 97 to the positive (+) input of voltage comparator 94, which signal is essentially zero when the force being applied to the muscle is less than $F_{min}$, is more positive than the negative voltage signal being provided to the negative (−) input of such voltage comparator, the output produced by voltage comparator 94, which output is provided via lead 104 to the reset (R) input of flip-flop 112, will be HI and will remain HI until such time as the signal provided to the positive (+) input of such voltage comparator goes more negative than the negative signal provided to the negative (−) input thereof. As will be detailed more specifically with respect to FIG. 5, the output of comparator 86 is AC coupled to the set input of flip-flop 112. Accordingly, only the negative going edge, HI to LO transition, is coupled to the set input and no signal level is held at the set input to flip-flop 112 once it is triggered.

The presence of a LO signal at the set (S) input of flip-flop 112 and a HI signal at the reset (R) input thereof results in the production of a HI signal on the Q output thereof, which HI signal is provided to the control input 146C of switch 146 and to input 143 of the inverter-delay means 144. The HI signal at the control input 146C of switch 146 causes switch 146 to remain closed, as a consequence of which the signal at output 141 of divider means 140 is communicated through switch 146 to charge capacitor 158 and is provided therefrom to data input 165 of display 164. The presence of a HI signal at input 143 of inverter-delay means 144 causes the output of such inverter-delay means to go LO and to remain LO until such time as the Q output of flip-flop 112 subsequently goes LO.

In light of what has previously been discussed herein with regard to display 164, it will thus be apparent that, so long as the force being applied to the muscle under study is below the value of $f_{min}$, display means 164 will not operate to produce displayed values corresponding to the data then being supplied to the data input 165 of the display means.

For the sake of completeness of description, it may be observed that switch 126, capacitor 128, buffer 130, and differential amplifier 132 operate in similar fashion to switch 82, capacitor 85, buffer 87, and differential amplifier 97, so long as the force being applied to the muscle under study is below the value of but, as should be clear from the discussion hereinbefore, the effect of such operation is of little consequence during such time.

As increasing force is applied to the muscle under study by applying pressure to the trigger 18 to squeeze the muscle between the tong arm portions 14A and 16A, the applied force is detected by transducer means 70 and is amplified and provided via leads 78 and 80 to the inverting (−) input of differential amplifier 97. As such increasing force is being applied to the muscle, and is detected by force transducer means 70, displacement transducer 116 detects the displacement of the tong arms 14 and 16 resulting from such applied force and generates an analog signal which is amplified by amplifier 120 and provided via lead 124 to the inverting (−) input to differential amplifier 132. When the voltage signal provided via lead 76 to the negative (−) input of voltage comparator 86 eventually becomes more positive than the voltage input being provided to the positive (+) input thereof, i.e., when the force being applied to the muscle exceeds $f_{min}$, the output of voltage comparator 86, which output is provided to the set (S) input of flip-flop 112 and to the control inputs 82C and 126C of switches 82 and 126, causes flip-flop 112 to be set and its Q output to go HI, and causes both of switches 82 and 126 to open, thereby interrupting further communication of signals through such switches, as a consequence of which the values stored on capacitors 85 and 128 at the time the switches 82 and 126 open will continue to be provided to respective non-inverting (+) inputs of differential amplifiers 97 and 132 through buffers 87 and 130, respectively. Consequently, once switches 82 and 126 open, differential amplifiers 97 and 132 operate to produce non-zero difference output signals representative of the differences between the voltage values applied to their respective inputs. As the applied force increases, the difference output signal ΔF from differential amplifier 97 therefore becomes increasingly negative, and as the displacement increases, the difference output signal ΔD from differential amplifier 132 also becomes increasingly negative.

As has been noted, the difference output signals ΔF and ΔD are supplied to analog divider means 140. Such divider means operates at any given point in time to produce at its output 141 a voltage signal, defined to be ΔF/ΔD, that is proportional to the value of the ΔF signal then being supplied divided by the value of the ΔD signal then being supplied. Since Q output of flip-flop 112 is HI at such time, switch 146 remains closed, as a consequence of which capacitor 168 is charged by the ratio output signal from analog divider means 140. Since the signal at output 145 of inverter delay means 144 remains LO, display 164 remains enabled during such time permitting updated displays to be produced thereby.

Eventually, however, as the force applied to the muscle under study is increased, the difference output signal produced at output 98 of differential amplifier 97 becomes so negative that it drops below the value of the signal being supplied to the negative (−) input of voltage comparator 94, as a consequence of which the output of voltage comparator 94 goes LO. Such LO signal is provided via lead 104 to the reset (R) input of flip-flop 112, and, since no change in signal is then being provided to the set (S) input of such flip-flop, flip-flop 112 operates to cause the signal on the Q output thereof to change from a HI to a LO. Such Lo signal is provided to control input 146C of switch 146 as well as to input 143 of inverter-delay means 144. The presence of a LO signal at input 146C of switch 146 causes such switch to open, thereby preventing communication between sides 146A and 146B of switch means 146 and preventing any further charging of capacitor 168.

Thereafter, until switch 146 is again closed, the signal being provided to data input 165 display means 164 is the value of the charge stored on capacitor 168. Inverter-delay means 144 responds to the change from a HI to a LO signal at input 143 thereof to produce, after a suitable delay, a change from a LO to a Hi signal at output 145, which change in state is detected at trigger or hold input 163 of display 164.

It will be appreciated by those skilled in the art that the noted delay time is chosen to be sufficiently long enough to permit switch 146 to open when the divider output signal present at the switch and capacitor 168 is the muscle tone value calculated with the upper threshold force and displacement values. When the positive going edge has been detected on trigger or hold input 163 of display 164.

Display 164 now operates to freeze or hold the display value at a value corresponding to the data signal being provided to data input 165 from capacitor 168. It will be appreciated that once switch means 146 opens in response to the production of a LO signal at the Q output of flip-flop 112, thereby preventing further communication of ratio output signals from divider means 140 to capacitor 168 and display means 164, any further increase in the application of force to the muscle will be to no avail, at least for purposes of obtaining muscle tone measurements.

When a muscle tone measurement is completed and trigger 18 (FIG. 2) is released, spring arms 58A and 58B of spring 58 cause the rear ends 14D and 16D of tong arms 14 and 16 to move away from one another, thereby causing the muscle contactor portions 14A and 16A of such tong arms to move out of contact with the muscle body and causing pulley 32 to rotate in a clockwise direction. As the force being applied to the muscle body decreases, the voltage signal being applied to the inverting (−) input of differential amplifier 97 likewise decreases and begins to approach the value stored on capacitor 85, as a consequence of which the value of the difference output signal at output 98 of differential amplifier 97, which signal is being supplied to the positive (+) input of voltage comparator 94, becomes less and less negative. When such difference output signal becomes less negative than the voltage signal being provided to the negative (−) input of voltage comparator 94, the output 95 of such voltage comparator 94 returns HI.

When the applied force has decreased sufficiently to fall below $f_{min}$ due to the release of trigger 18, the voltage at the positive (+) input of voltage comparator 86 once again exceeds the voltage at the negative (−) input thereof, as a consequence of which the output of voltage comparator 86 returns to its initial HI state. The return of such output signal, which is provided to control inputs 82C and 126C of switch means 82 and 126 and to the set (S) input of flip-flop 112, to a HI state causes switch means 82 and 126 to again close. Those skilled in the art will recognize that there is provided in association with switch means 82 and 126, and the capacitors 85 and 128, associated, respectively, therewith, suitable circuitry to allow the capacitors to discharge when the switch means are closed.

From the foregoing, it will be appreciated that the release of the trigger 18 thus effects operation of the noted circuitry to reinitialize such circuitry for future muscle tone measurement operations.

Those skilled in the art will recognize that FIG. 5 is a more detailed schematic that depicts in greater detail particular circuitry that might be employed to construct an embodiment in accordance with FIG. 4, which detailed schematic includes certain optional features not shown in FIG. 4. Such features and the purposes therefor will become apparent in that which follows.

The circuit of FIG. 5 includes a Wheatstone bridge strain gage transducer 70, which, by way of example, may be a Micro-Measurements Model EA-06-12582-350W Transducer, detection terminals 172 and 174 of which are operatively connected, as shown, to amplifier means 74, which amplifier means may take the form depicted. In operation, when a muscle is squeezed between the caliper arms 14 and 16, the individual caliper arms bend outward at the reduced cross-sectional areas 21-24 thereof in response to the resistive force of the muscle. Such bending compresses sensors 37 and 34 while expanding sensors 35 and 36. The relative expansion and contraction of the sensors results in changes in the output voltage signals provided via leads 172 and 174 to amplifier means 74. Such change in voltage corresponds to the amount of force applied to the particular muscle body positioned between the caliper arms. If the pressure being exerted is subsequently released, the compressed sensors 37 and 34 will expand and the expanded sensors 36 and 35 will contract and return to their initial states, as a consequence of which the output voltage signals will revert to their initial values. Amplifier means 74 operates in accordance with the discussion previously presented with regard to FIG. 4 so as to produce at output 178 thereof an amplified force detected signal, which signal is provided through lead 250, resistor 228 and lead 226 to the inverting (−) input of differential amplifier 220, through leads 250 and 252 to the negative (−) input of voltage comparator 282, and to the first side 82A of switch means 82. The second side 82B of switch means 82 is connected, in common, to grounded capacitor 85 and through resistor 210 to the non-inverting (+) input of operational amplifier 212, connected as a voltage follower so as to act as buffer, the output 213 of which is connected through a voltage divider circuit including resistors 216 and 218 to the non-inverting (+) input of differential amplifier 220.

The displacement transducer 32 of FIG. 2 is depicted in FIG. 5 as a potentiometer 184 connected between ground and a positive voltage source. The adjustable contact 234 thereof is connected through resistor 236 to the non-inverting (+) input of operational amplifier 238, which is shown connected as a voltage follower. The output voltage signal of potentiometer 184 is proportional to the displacement of the caliper arms, and operational amplifier 238 buffers such voltage signal before providing it via lead 242, resistor 288 and lead 262 to the inverting (−) input of differential amplifier 260 and via lead 244 to the first side 126A of switch means 126, the second side 126B of which is connected, in common, to grounded capacitor 128 and through resistor 247 to the non-inverting (+) input of operational amplifier 252, connected as a voltage follower so as to act as a buffer, the output 253 of which is connected through a voltage divider circuit including resistors 256 and 258 to the non-inverting (+) input of differential amplifier 260.

The ΔF output signal produced at output 221 of differential amplifier 220 is provided via leads 223 and 227 and through one or both of resistors 224 and 225 to pins 1 and 14, as shown, of voltage divider circuit 296, which circuit is depicted in FIG. 5 as an XR2208 Analog Divider manufactured by EXAR Integrated Systems, Inc., connected as shown. As so depicted, pin 3 of such Analog Divider is connected to receive the ΔD output signal produced at output 261 of differential amplifier 260, and such Analog Divider so operates to produce at the adjustable contact 391 of a voltage divider circuit that includes resistors 390, 394, and 396 a ratio output signal corresponding to ΔF/ΔD.

The reference adjustment means 88 of FIG. 2 includes a potentiometer 267 connected in series with resistor 266 between ground and a positive voltage source, the adjustable contact 268 of which potentiometer is connected through resistor 280 to the positive (+) input of voltage comparator 282 and via lead 306 to inverting amplifier means 92, which amplifier means may be constructed as shown to have a selectable gain depending upon the position of switch 316, the purpose and operation of which will be described hereinafter. The output 283 of voltage comparator 282 is connected through pull-up resistor 371 and light emitting diode 373 to a positive voltage source, and the signal produced thereat is provided via leads 286, 287 and 206 to control input 82C of switch means 82, via lead 286 and 248 to control input 126C of switch means 126, and via leads 286, 287 and 289 to flip-flip 112.

Inverting amplifier means 92 is depicted as including an operational amplifier 330, the inverting (−) input of which is connected via lead 306 and resistor 308 to receive the reference voltage signal established at adjustable contact 268 of potentiometer 267, and the non-inverting (+) input of which is connected to ground. The output 336 of such operational amplifier 330 is shown connected back to the inverting (−) input through one of two feedback loops, i.e., either the loop including variable resistor 322 and resistor 314 or the loop including variable resistor 324 and resistor 314, depending upon the position of switch 316. Operational amplifier 330 amplifies the reference voltage signal established by reference adjustment means 88 and permits adjustment of the amplification to establish a second reference signal corresponding to an upper limit of applied force, defined as $f_{max}$. The total resistance in each feedback loop determines the gain of amplifier 330. When switch 316 is moved to contact 318, the signal produced at output 336 corresponds to an upper limit reference value for high tone muscles, and when switch is moved to contact 320, the signal produced corresponds to an upper limit reference value for low tone muscles.

The output 336 of inverting amplifier means 92 is connected to the negative (−) input of voltage comparator 340, the positive (+) input of which is connected to receive via leads 223 and 333 and through resistor 334 the ΔF signal produced at output 221 of differential amplifier 220, and the output 341 of which is connected through pull-up resistor 348 to a positive voltage source. The signal produced at such output is provided to input 342 of flip-flip 112.

It will be readily appreciated by those skilled in the art that the circuitry depicted in block 112, although not a flip-flop in the classic sense, operates in such a fashion when connected as shown to be treated as and to be considered to be a set-reset flip-flop. Such circuitry includes a voltage comparator 358, the negative (−) input of which is AC coupled through capacitor 357 to the output 283 of voltage comparator 282. As discussed earlier herein, the AC coupling limits triggering to the LO-going transitional edge. The HI-going edge is clamped to ground by diode 361 and thus has no effect on the negative (−) input of voltage comparator 358. The positive (+) input of comparator 358 is operatively connected as shown to the output 341 of voltage comparator 340, and the output 359 of which is connected through pull-up resistor 376 and light emitting diode 377 to a positive voltage source. The signal produced at such output 359 is provided via lead 382 to control input 146C of switch means 146, via lead 375 to input 378 of an inverter-delay means 144 constructed as shown, and via leads 375 and 379 to an audio signal means 381 that includes a voltage comparator 370.

The various voltage comparators depicted in FIG. 5 each function in such a manner that the output thereof is pulled HI by virtue of the presence of a pull-up resistor connected to a positive voltage source, unless the voltage present at the negative (−) input thereof is greater, i.e., more positive, than the voltage present at the positive (+) input thereof, thereby causing the output to go LO. Consequently, the light emitting diodes 373 and 377 associated with voltage comparators 282 and 358, respectively, will turn ON whenever the voltage present at the negative (−) input of such voltage comparator becomes more positive than the voltage present at the positive (+) input. In light thereof, and in view of the discussion with respect to FIG. 4, it will be readily understood that light emitting diode 373 turns ON whenever the lower force limit is exceeded and that light emitting diode 377 turns ON whenever the upper force limit is exceeded. Such light emitting diodes 373 and 377 may be so positioned, as indicated in FIG. 3, to provide visual indications to the user of the status of the muscle tone measurement operation.

With the embodiment of FIG. 5, once the upper force limit $f_{max}$ is exceeded, usable data is no longer being obtained. As an aid to the operator, the audio signal means 381 is connected to provide an audio signal to the operator when such force limit is exceeded so that the operator can then terminate further force application. When the output 359 of voltage comparator 358 goes LO, such LO signal is coupled to the positive (+) input of comparator 370 via capacitor 366. The positive (+) input of comparator 370 is normally held HI by resistor 368 connected to a positive voltage supply. When the HI to LO transition produced at output 359 of voltage comparator 358 is coupled through capacitor 366, the positive (+) input of comparator 370 is pulled LO for a brief period, typically about 0.3 seconds, as a consequence of which the output of comparator 370 is driven LO for that same time period, thus causing the audio alarm 171 connected between the output of comparator 370 and a positive voltage source to turn ON for such time period. Such audio alarm thus operates to notify the operator that the muscle tone measurement has been completed.

From the foregoing, it should now be readily apparent to those skilled in the art that the embodiment depicted in FIG. 5 operates in accordance with the operational discussion previously presented with regard to FIG. 4.

Figure 6:
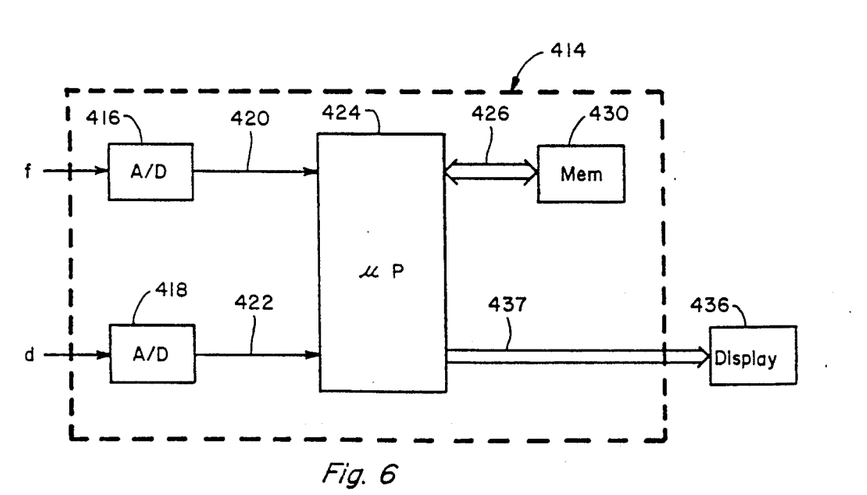
FIG. 6 is a block diagram depicting the major components of an alternative embodiment of the invention, which utilizes a microprocessor.

FIG. 6 depicts in block diagram form an alternative embodiment of the present invention, which embodiment is offered for illustrative purposes only, and not by way of any limitation. In the FIG. 6 embodiment, the circuitry of block 81 in FIG. 4 has been replaced by a control section 414 that includes analog-to-digital converters 416 and 418 operatively connected to receive and convert to digital signals the analog force and displacement signal inputs, which digital signals are provided to a microprocessor 424 via leads 420 and 422. A memory means 430 is shown connected to microprocessor 424 via bus line 426 and display means 436 is shown connected to microprocessor 424 via path 437 to receive data and control signals therefrom.

Figure 7:
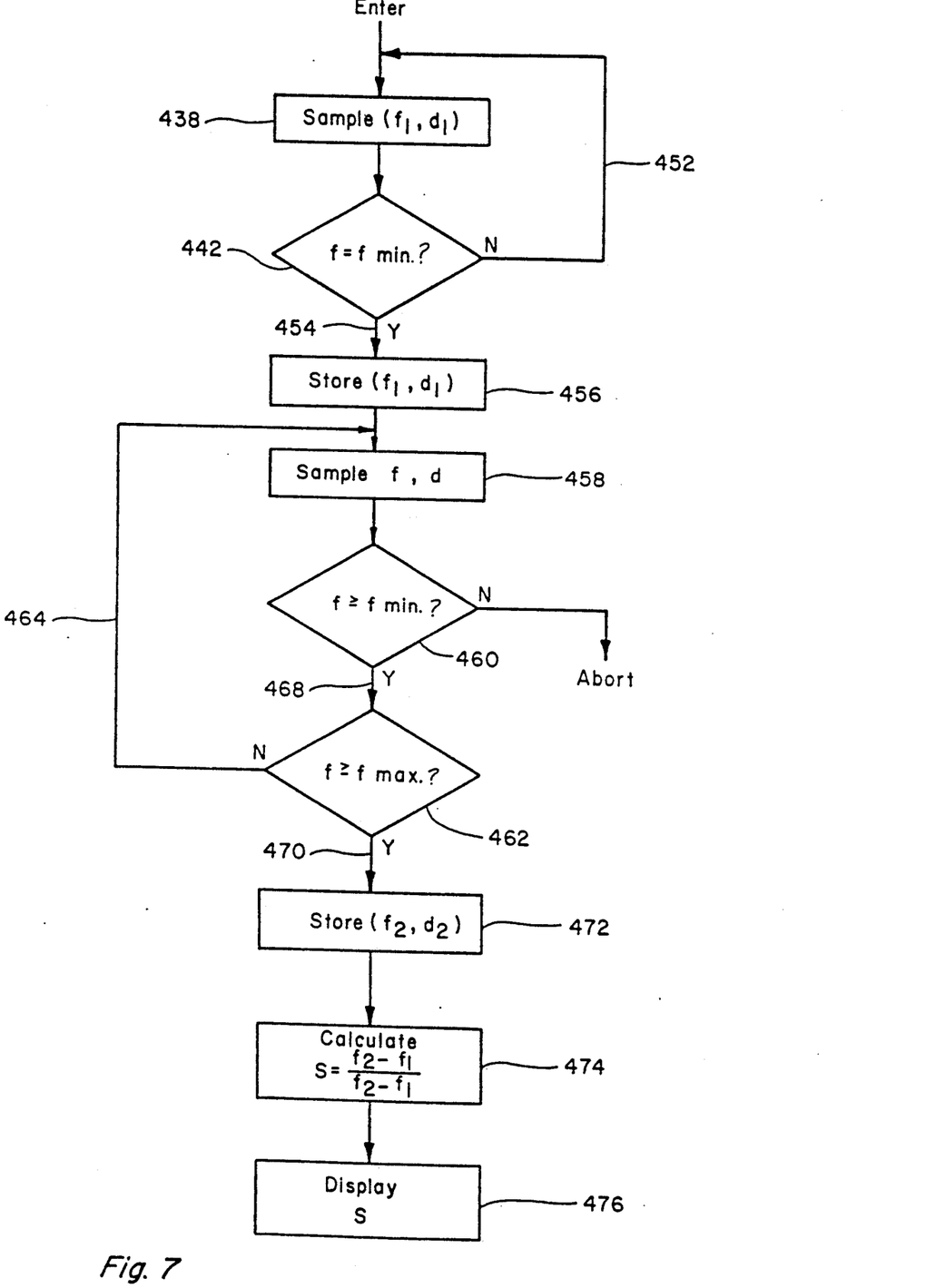
FIG. 7 is a flow chart depicting a portion of a typical operational sequence of the embodiment of FIG. 6.

FIG. 7 depicts a portion of a typical operational sequence such as might be followed by the embodiment of FIG. 6. It will be readily apparent that the microprocessor control means 424 of FIG. 6 may be readily programmed to function during a muscle tone measurement operation by entering a loop sequence, including blocks 438 and 442 and branch 452, in accordance with which it effects sampling of force and displacement values by any of various means or techniques, as noted in block 438, and thereafter checks to determine whether the sampled force value is greater than or equal to a minimum force reference value $f_{min}$, as noted in block 442. If the sampled force value is not greater than or equal to the minimum force reference value $f_{min}$, a new sample is taken, as denoted by branch 452 from block 442 back to block 438. Such operational loop will continue until a sampled force greater than or equal to $f_{min}$ is detected. Once the sampled force is found to be greater than or equal to the minimum force reference value, the operational sequence exits the noted loop and follows branch 454 from block 442 to block 456, in accordance with which microprocessor 424 will then operate to store the sampled force and displacement values as a first point pair ($f_1$, $d_1$) before entering another sample and check sequence loop including blocks 458, 460, and 462 and branch 464.

Within such noted loop, microprocessor 424 effects the sampling of force and displacement values in accordance with block 458 and then checks to determine whether the sampled force value is greater than or equal to the minimum force reference value $f_{min}$, as noted in block 460. If the sampled force is not greater than or equal to such minimum force reference value, such as would be the case if the trigger 18 of the tonometer device were released prior to completion of a muscle tone measurement, the operational sequence would follow path 466 from block 460 and enter an abort or error routine, as noted. If the sampled force is greater than or equal to the minimum reference value force $f_{min}$, however, the operational sequence instead proceeds along branch 468 from block 460 to block 462 in accordance with which the microprocessor acts to check the sampled force value to determine if it is greater than or equal to a maximum force reference value $f_{max}$. If not, the operational sequence follows branch 464 from block 462 back to block 460 and remains in the noted sampling and checking loop. On the other hand, if the sampled force is greater than or equal to the maximum force reference value $f_{max}$, the operational sequence follows branch 470 from block 462 and exits such sampling and checking loop.

Upon exiting the noted sampling and checking loop, microprocessor 424 operates in accordance with block 472 to store the last sampled force and displacement values as point pair ($f_2$, $d_2$) and thereafter operates in accordance with blocks 474 and 476 to calculate a muscle tone measurement defined as $S = \Delta F/\Delta D = (f_2 - f_1)/(d_2 - d_1)$, and to then display such calculated value.

It will be appreciated by those skilled in the art that with the embodiment of FIG. 6 the microprocessor could be so programmed to automatically determine when the sampled data is data obtained within the elastic region of the muscle, and to make use of data obtained from the elastic region of such muscle to derive a muscle tone measurement. As may be observed from FIG. 1, the force-displacement curve is non-linear between points B and C, becomes relatively linear between points C and D, and experiences a change in linearity above point D. It is possible to make use of such observations by monitoring the outputs of the force and displacement transducers during a muscle tone measurement operation and determining by appropriate algorithms when the monitored measurements define a relatively linear region, e.g., a line of substantially uniform slope, between a non-linear portion (below point B) and a significant change in slope (above point D). Such automatic detection can be accomplished by means of various programming techniques and algorithms utilized by those skilled in the art of programming.

It will also be appreciated by those skilled in the art that the microprocessor embodiment of the present invention could also be so programmed to automatically compare the shape of the force versus displacement curve with a library of such curves for different muscle types, i.e., low, normal, and high tone muscle groups, and, from such comparison, determine which muscle type or category the particular muscle being measured corresponds to. Such microprocessor could likewise be programmed to use a variety of different computational techniques for making this comparison. For example, the microprocessor could determine if the particular muscle being studied is a normal or low tone muscle and, thereafter, select the appropriate upper force threshold value for such muscle. It is also recognized that a multitude of muscle categories can be identified and programmed into the microprocessor in addition to the muscle categories set forth in the present application. The microprocessor could also be programmed to store a multitude of points associated with the force versus displacement curve, and make the $\Delta F/\Delta D$ computation based upon such multitude of data points. Furthermore, the microprocessor could also be programmed to fit a polynomial curve to the force versus displacement data received and, thereafter, determine the curve equation for the particular muscle under study and calculate a muscle tone value from such equation. Alternatively, the microprocessor could be programmed to compare the particular force versus displacement curve equation associated with the muscle under study to a library of such curve equations previously obtained for muscles of known tone condition and, thereafter, select a particular muscle tone value based upon the most similar stored equation. Still further, the microprocessor could be programmed so that the various data points on the particular force versus displacement curve would be weighted before any computations are made thereby making some data points more important than others. All of the above noted capabilites are illustrative of some of the various ways the microprocessor of the present unit can be programmed to determine the appropriate muscle tone value and such listing should not be considered exhaustive.

Figure 8:
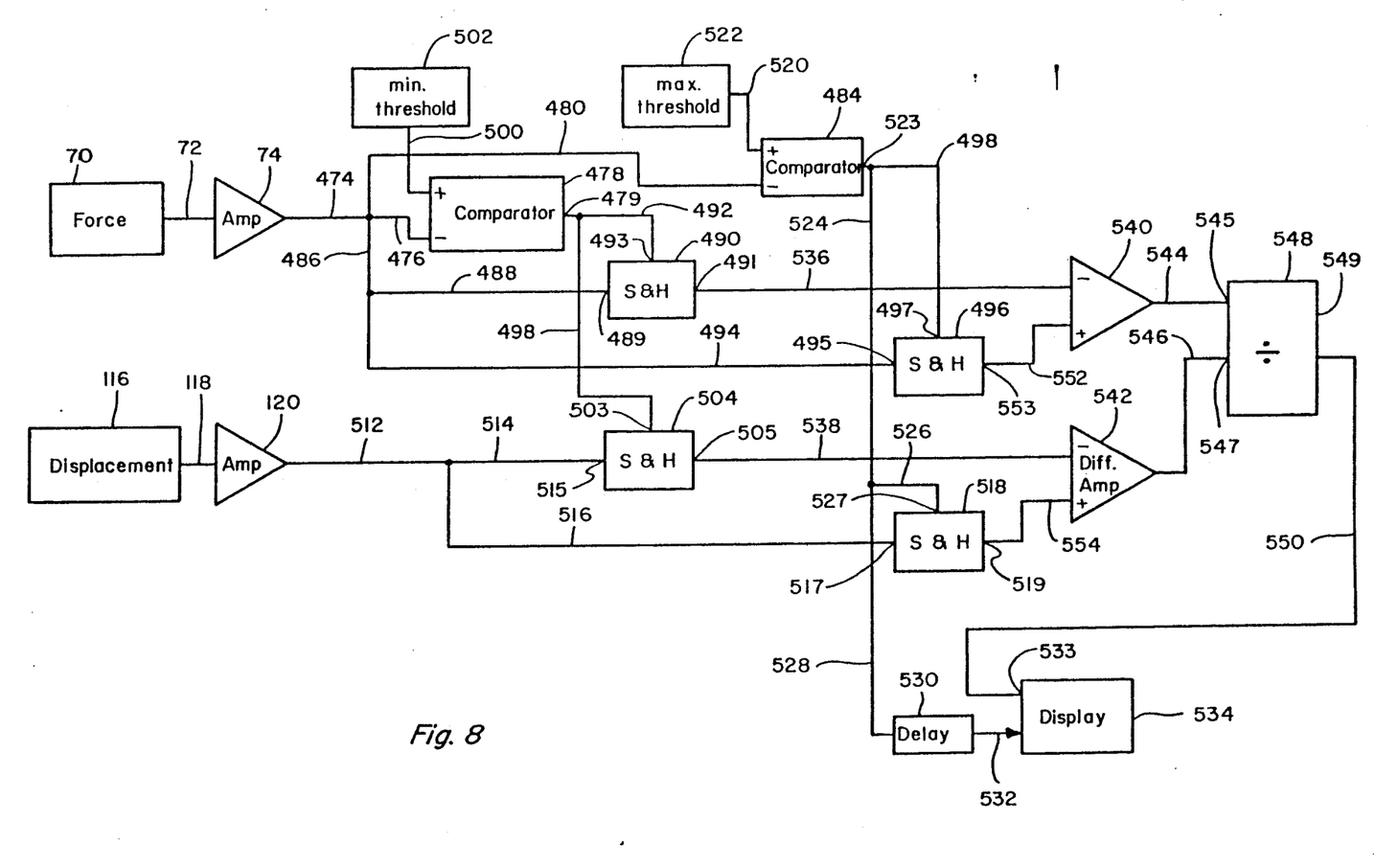
FIG. 8 is a block diagram depicting the major components of another alternative embodiment of the invention, which utilizes sample and hold circuits.

FIG. 8 identifies another possible alternative embodiment of the invention, which embodiment is offered for illustrative purposes only, and not by way of any limitation. In the FIG. 8 embodiment, the force signal from transducer 70 is provided via lead 72 to an amplifier 74 which amplifies such signal and thereafter provides such amplified signal to several locations, including via leads 474 and 476 to the negative (−) input of a comparator 478, via leads 474 and 480 to the negative (−) input of a comparator 484, via leads 474, 486 and 488 to the input 489 of a sample and hold circuit 490, and via leads 474, 486 and 494 to the data input 495 of a sample and hold circuit 496. The positive (+) input of comparator 478 is connected to receive via lead 500 an $f_{min}$ input from a minimum threshold reference value adjustment means 502, and the output 479 of such comparator 478 is connected via lead 492 to the control input 493 of sample and hold circuit 490 and via lead 498 to the control input 503 of sample and hold circuit 504.

The displacement signal from displacement transducer 116 is provided via lead 118 to an amplifier 120 which amplifies such signal and thereafter provides such amplified signal via leads 512 and 514 to the data input 515 of sample and hold circuit 504 and via leads 512 and 516 to the input 517 of a sample and hold circuit 518. The positive (+) input of comparator circuit 484 is connected to receive via lead 520 an $f_{max}$ input from a maximum threshold reference value adjustment means 522, and the output 523 of such comparator 484 is connected via lead 498 to the control input 497 of sample and hold circuit 496 and via leads 524 and 526 to the control input 527 of sample and hold circuit 518. Such output 523 is also connected via leads 524 and 528 to delay means 530, which means operates to briefly delay any signal change communicated thereto before providing such signal via lead 532 to display means 534.

The output 491 of sample and hold circuit 490 is connected via lead 536 to the inverting (−) input of a differential amplifier 540, the non-inverting (+) input of which is connected via lead 552 to the output 553 of sample and hold means 496. Similarly, the output 505 of sample and hold means 504 is connected via lead 538 to the inverting (−) input of differential amplifier 542, the non-inverting (+) input of which is connected via lead 554 to the output 519 of sample and hold means 518.

It will be readily understood by those skilled in the art that each of the noted sample and hold circuits may be constructed to respond to a LO signal provided to its control input to sample and hold the signal then being provided to its data input. It will be further appreciated that the output signal produced by differential amplifier 540 corresponds to the difference force signal $\Delta F$, which signal is provided via lead 544 to the dividend input 545 of divider means 548, and that the output signal produced by differential amplifier 542 corresponds to the difference displacement signal $\Delta D$, which signal is provided via lead 546 to the divisor input 547 of divider means 548, the output 549 of which divider means 548 is connected via lead 550 to the input 533 of display means 534.

In operation, when the input force signal applied to comparator 478 exceeds the minimum threshold value $f_{min}$, the output of comparator 478 changes state, thus activating sample and hold circuits 490 and 504 and thereby effecting a sampling of the force signal present at input 489 of sample and hold circuit 490 and the displacement signal present at input 515 of sample and hold circuit 504, which sampled values are then held by such sample and hold means at the respective outputs 491 and 505 thereof and provided to the inverting (−) inputs of differential amplifiers 540 and 542. When the applied input force signal reaches the maximum threshold reference value $f_{max}$ established by reference threshold adjustment means 522, the output of comparator 484 changes state thus activating sample and hold circuits 496 and 518, which circuits operate to sample the force and displacement signals then present at repsective inputs 495 and 517 thereof and to hold such sampled values at outputs 553 and 519 so that they can be provided to the non-inverting (+) inputs of differential amplifiers 540 and 542. Differential amplifier 540 operates to produce a $\Delta F$ value when the applied force exceeds the maximum threshold value $f_{max}$ and differential amplifier 542 operates to produce a $\Delta D$ value, the values of which are utilized by divider means to produce a $\Delta F/\Delta D$ signal at output 549 thereof. Delay means 530 serves to delay enablement of display means 534 a sufficient amount of time to allow the divider means 548 to calculate and provide the quotient $\Delta F/\Delta D$ via lead 550 to the display means.

Thus there has been shown and described a novel muscle tonometer apparatus and a method for using same, which muscle tonometer apparatus and method fulfill the various objects and advantages sought therefor. It will be apparent to those skilled in the art, however, that many changes, modifications, variations, and other uses and applications for the subject means and method are possible and contemplated, and all such changes, modifications, variations, and other uses and applications which do not depart from the spirit and scope of the invention are deemed to be covered by the invention, which is limited only by the claims which follow.

I claim:

1. Apparatus for quantifying the tone of a muscle by measuring the ratio of a change of force applied to the muscle and the resulting change in displacement of the muscle for forces applied to the muscle over a linear region of a force/displacement curve, such region representing the elastic region of the muscle, said apparatus comprising: force-applying means for applying a variable force to the muscle to effect a corresponding displacement of the muscle; force transducer means mechanically coupled to said force-applying means for producing an electric force signal representative of the instantaneous forces applied to the muscle thereby; displacement transducer means mechanically coupled to said force-applying means for providing an electric displacement signal representation of the corresponding instantaneous muscle displacements caused by such instantaneous forces; and electronic circuitry connected to said force and displacement transducer means including, first circuit means coupled to said force transducer means for producing a minimum force signal at a predetermined minimum force level of said linear region, second circuit means coupled to said displacement transducer means for producing a minimum displacement signal representative of the minimum muscle displacement corresponding to said minimum force signal, first differential means coupled to said force transducer means and to said first circuit means for producing a first output signal representative of the instantaneous differentials of increased forces with respect to said minimum force signal, second differential means coupled to said first displacement transducer means and to said second circuit means for producing a second output signal representative of the instantaneous differentials of corresponding muscle displacements with respect to said minimum muscle displacement, divider means coupled to said first and second differential means for dividing said first output signal with said second output signal to produce a ratio output signal, display means for displaying indications of the amplitude of said ratio output signal, further circuit means connecting said display means to said divider means, and control circuit means connected to said display means for terminating the introduction of said ratio signal from said dividing means to said display means at a predetermined maximum force level of said linear region greater than said minimum force level, so that said display means displays an indication of the amplitude of said ratio signal at predetermined force level representing the slope of the linear region of said force/displacement curve and providing an indication of the tone value of the muscle.

2. The apparatus as defined in claim 1, in which said first circuit means includes manually adjustable means for setting said minimum predetermined force level.

3. The apparatus defined in claim 1, in which said control circuit means is coupled to said first circuit means for deriving a control signal for terminating the introduction of said ratio signal from said divider means to said display means at said predetermined maximum force level.

4. The apparatus defined in claim 3, and which includes operator adjustable means for setting said minimum and maximum predetermined force levels.

5. The apparatus defined in claim 1, in which said control circuit means includes storage means for applying a constant amplitude signal to said display corresponding to the amplitude of said ratio signal at said predetermined maximum force level after the termination of the introduction of said ratio signal from said divider means to said display means.

6. The apparatus defined in claim 1, said including processing means, said processing means includes a microprocessor and memory means associated therewith, said memory means being operatively connected to said microprocessor to permit the storage of data therein by said microprocessor and the retrieval therefrom of such data by said microprocessor.

7. The apparatus defined in claim 6, in which said predetermined minimum and maximum force levels are pre-established values stored in said memory means.

8. The apparatus defined in claim 6, in which said microprocessor is operatively connected to receive force and displacement values and is programmed to (a) detect and store the values of a first force-displacement signal pair the value of whose force signal is greater than or equal to the predetermined minimum force level, (b) subsequently detect and store the values of a second-force displacement signal pair the value of whose force signal is less than or equal to said maximum predetermined force level, (c) calculate the ratio of the difference in value of the first signals of said first and second force-displacement signal pairs to the difference in value of the displacement signals of said first nd second force-displacement signal pairs and provide a ratio output signal corresponding to said calculated ratio to said display means, and (d) effect the display of the muscle tone measurement by said display means.

9. The apparatus defined in claim 6, in which said microprocessor is operably connected to receive force and displacement values and is programmed to (a) sample force and displacement values until a relatively linear relationship is detected in successively sampled force-displacement signal pairs to establish said predetermined minimum force level (b) subsequently sample force and displacement values until a substantial deviation from said detected relatively linear relationship is detected in successively sampled force-displacement pairs to establish said predetermined maximum force level, (c) provide to said display means a signal representative of said detected relatively linear relationship, said signal being said ratio output signal, and (d) effect the display of the muscle tone measurement by said display means.

10. The apparatus defined in claim 1, in which said force-applying means comprises a hand-held manually operable instrument which includes a portable body unit, said body unit having movable caliper arms pivotally coupled thereto and extending therefrom, and a trigger assembly coupled to said caliper arms to control the movement of said caliper arms, said caliper arms being configured to apply compressive forces to a muscle positioned therebetween when said trigger assembly is actuated by pressure applied thereto, said force-applying means including said caliper arms.

11. The apparatus defined in claim 10, in which said display means is mounted on said body unit and said electronic circuitry is encompassed within said body unit.

12. A method of obtaining a muscle tone measurement by measuring the ratio of a change of force applied to the muscle and the resulting change in displacement of the muscle for forces applied to the muscle over a linear region of a force/displacement curve, such region representing the elastic region of the muscle, comprising the steps of
 a) providing a muscle tone measurement means including means for monitoring the amount of force applied to a muscle and the displacement of the muscle resulting therefrom;
 b) applying an increasing force to a muscle to effect displacement thereof in accordance with the amount of force applied until the force value exceeds a specified minimum force value at a predetermined minimum force level of said linear region;
 c) determining for two applied force values between the specified minimum force value and a specified maximum force value at a predetermined maximum force level of said linear region greater than said minimum force level the displacements effected by such force values, the values of the force applied and the muscle displacement from a reference state resulting therefrom defining two force-displacement value pairs whereby each applied force value has associated therewith a displacement value;
 d) calculating the ratio of the difference in value of the force values of said two force-displacement value pairs to the difference in value of the displacement values of said two force-displacement value pairs, said ratio corresponding to the muscle tone of the muscle.

13. The method of claim 12 wherein the muscle tone measurement device provided in step a) includes a force application means operable by a user to apply force to a muscle and step b) includes the steps of
 1) locating, on the subject to be studied, the bony landmarks which represent the origin and insertion of the muscle whose tone is to be measured,
 2) locating the muscle portion between the bony landmarks that provides the greatest area of muscle bulk most free from hard cells,
 3) positioning the force application means to apply force to said muscle portion, and
 4) effecting operation of said force application means.

14. A method of obtaining a muscle tone measurement by measuring the ratio of a change of force applied to the muscle and the resulting change in displacement of the muscle for forces applied to the muscle over a linear region of a force/displacement curve, such region representing the elastic region of the muscle, comprising the steps of
 a) providing a muscle tone measurement means including means for monitoring the amount of force applied to a muscle and the displacement of the muscle resulting therefrom;
 b) applying an increasing force to a muscle to effect displacement thereof from a reference state in accordance with an amount of force applied until the force exceeds a specified minimum force at a predetermined minimum force level of said linear region;
 c) determining for a first applied force equal to said specified minimum force the displacement from the reference state effected thereby, the value of the force applied and the muscle displacement resulting therefrom defining a first force-displacement value pair;
 d) applying an increasing force to the muscle until the force equals a specified maximum force at a predetermined maximum force level of said linear region greater than said minimum force level;

e) determining for said last named force the displacement from said reference state effected thereby, the value of said last named force applied and the muscle displacement from said reference state resulting therefrom defining a second force-displacement value pair; calculating the ratio of the difference in value of the force values of said first ad second force-displacement value pairs to the difference in value of the displacement values of said first and second force-displacement value pairs, said ratio corresponding to the muscle tone of the muscle.

15. A method of obtaining a muscle tone measurement, comprising the steps of
    a) providing a muscle tone measurement means including means for monitoring and sampling the amount of force applied to a muscle and the displacement of the muscle resulting therefrom from an initial state prior to the application of force to the muscle, the force and displacement values for any given time defining a force-displacement value pair whereby each force value has associated therewith a displacement value from a reference state;
    b) applying an increasing force to said muscle to effect displacement thereof from said reference state in accordance with the amount of force applied;
    c) sampling force and displacement values until a relatively linear relationship is detected in successively sampled force-displacement value pairs to establish a minimum force value;
    d) subsequently sampling force and displacement values until a substantial deviation from said detected relatively linear relationship is detected in successively sampled force-displacement value pairs to establish a maximum force value;
    e) determining a muscle tone measurement from and corresponding to said detected relatively linear relationship.

* * * * *